(12) United States Patent
Kantamneni

(10) Patent No.: US 7,754,917 B2
(45) Date of Patent: Jul. 13, 2010

(54) PERFLUOROALKYL SUBSTITUTED ACRYLATE MONOMERS AND POLYMERS THEREOF

(75) Inventor: Shobha Kantamneni, Fairfax, VA (US)

(73) Assignee: Huntsman International LLC, The Woodlands, TX (US)

( * ) Notice: Subject to any disclaimer, the term of this patent is extended or adjusted under 35 U.S.C. 154(b) by 512 days.

(21) Appl. No.: 11/764,441

(22) Filed: Jun. 18, 2007

(65) Prior Publication Data

US 2008/0315147 A1 Dec. 25, 2008

Related U.S. Application Data

(62) Division of application No. 10/972,944, filed on Oct. 25, 2004, now Pat. No. 7,247,691.

(60) Provisional application No. 60/514,710, filed on Oct. 27, 2003.

(51) Int. Cl.
*C07C 231/02* (2006.01)
*C08F 18/20* (2006.01)

(52) U.S. Cl. .............. 564/133; 564/123; 564/134; 564/138; 564/143; 526/252; 526/245; 526/248; 526/255; 526/304; 526/307.3; 526/307.7; 526/329.4

(58) Field of Classification Search .......... 564/123, 564/133, 134, 138, 143; 526/252, 245, 248; 526/255, 304, 307.3, 307.7, 329.4
See application file for complete search history.

(56) References Cited

U.S. PATENT DOCUMENTS

| | | | |
|---|---|---|---|
| 3,271,430 A | 9/1966 | Teamac | |
| 3,498,958 A | 3/1970 | Chaudhuri et al. | |
| 3,567,500 A | 3/1971 | Moreau et al. | |
| 3,754,026 A | 8/1973 | Beyleveld et al. | |
| 3,769,307 A | 10/1973 | Moreau et al. | |
| 3,818,074 A | 6/1974 | Ahlbrecht | |
| 3,919,183 A | 11/1975 | Jager et al. | |
| 4,582,882 A | 4/1986 | Lynn et al. | |
| 4,606,973 A | 8/1986 | Schmidt et al. | |
| 5,663,273 A | 9/1997 | Haniff et al. | |
| 5,674,961 A | 10/1997 | Fitzgerald | |
| 5,876,617 A | 3/1999 | Sato et al. | |
| 6,153,675 A | 11/2000 | Yamamoto et al. | |
| 6,162,369 A | 12/2000 | Allewaert et al. | |
| 6,387,292 B1 | 5/2002 | Saito | |
| 6,566,470 B2 | 5/2003 | Kantamneni et al. | |
| 6,894,106 B2 | 5/2005 | Aga et al. | |

*Primary Examiner*—Helen L. Pezzuto

(57) ABSTRACT

Fluoroalkyl amidoalkyl alcohols of the formula

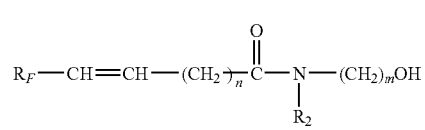

are disclosed and their corresponding (meth)acrylate esters. These fluoroalkyl amidoalkyl (meth)acrylate monomers can be copolymerized with a wide variety of conventional ethylenically unsaturated monomers. The resulting copolymers are useful as water, oil- and grease-proofing agents for paper, textiles and hard surfaces such as masonry and wood.

5 Claims, No Drawings

PERFLUOROALKYL SUBSTITUTED ACRYLATE MONOMERS AND POLYMERS THEREOF

CROSS REFERENCE TO RELATED APPLICATIONS

This application is a divisional of U.S. patent application Ser. No. 10/972,944, filed Oct. 25, 2004, now U.S. Pat. No. 7,247,691, which claims the benefit of priority of U.S. Provisional Pat. App. No. 60/514,710, filed Oct. 27, 2003. The noted applications are hereby incorporated by reference.

BACKGROUND AND PRIOR ART

The use of perfluoroalkyl- (in the following abbreviated as $R_F$-) substituted polymers to impart oil and water repellency to a variety of substrates such as textiles and paper is well known. The vast majority of these polymers are perfluoroalkyl-substituted acrylate copolymers useful for treating paper and paper products to impart oil and water repellency. U.S. Pat. No. 3,919,183 (Jager et al.) discloses polymers useful as oil repellant coatings for porous substrates such as textile materials and paper which comprise a perfluoroalkylethyl acrylate. U.S. Pat. No. 4,582,882 (Lynn et al.) describes fluorinated paper sizes which are copolymers of perfluoroalkyl acrylate. Also U.S. Pat. No. 5,674,961 of Fitzgerald discloses fluorochemical polymers useful for water, oil and grease resistance to paper. The monomers used to synthesize the above perfluoroalkylated polymers are derived exclusively from $R_F$-substituted alcohols where an ethylene group is present between the $R_F$ and the hydroxyl group.

Several patents also describe $R_F$-substituted polyurethanes, for example U.S. Pat. No. 5,663,273. Polyamide-amino polymers derived from polyethyleneimine by reaction with esters of perfluoroalkyl-substituted carboxylic acids are described in U.S. Pat. Nos. 3,769,307 and 3,567,500. These polymers contain a mixture of $R_F$-substituted amide and secondary amino groups. These polymers are used to impart oleophobicity yet hydrophilicity to textile substrates.

Di-$R_F$ amidomonocarboxylic acids prepared from 1 equivalent of diethylenetriamine, 2 equivalents of an $R_F$-acid and 1 equivalent of an anhydride are taught for use as textile finishes in U.S. Pat. No. 3,754,026. Similar $R_F$-amide-substituted polyethyleneimines useful as chemically resistant surfactants are described in U.S. Pat. No. 3,271,430. They are obtained by reaction of a perfluorinated alkanoic acid with a large excess of ethyleneimine. Reaction products of $R_F$-substituted acids with polymers bearing pendent primary amino groups attached to a carbon-carbon backbone by a linking group are claimed in U.S. Pat. No. 4,606,973 as low surface energy coatings for flat substrates.

U.S. Pat. No. 3,818,074 describes saturated and unsaturated fluorinated alcohols which can have 2 to 12 methylene groups separating a perfluoroalkyl radical having from three to 12 carbon atoms and the hydroxyl group.

U.S. Pat. No. 3,498,958, discloses perfluoroalkyl amidoalkyl alcohols which have 1 to 14 methylene groups separating the perfluoroalkyl radical and the amido group, (meth) acrylate esters thereof and copolymers derived therefrom. The amidoalkyl alcohols are the saturated analogues of the amidoalkanols of formula I described below, and are obtained by a different synthetic route.

SUMMARY OF THE INVENTION

One aspect of the present invention is a novel $R_F$-alcohol of formula I,

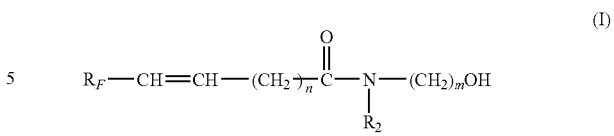

wherein
$R_F$ is a straight or branched-chain perfluoroalkyl group containing 4 to 20 carbon atoms,
$R_2$ is hydrogen or an alkyl group with 1 to 4 carbon atoms, and
m and n are, independently of each other, an integer from 2 to 11.

This $R_F$-alcohol of formula I is synthesized by reacting a linear terminally unsaturated monocarboxylic acid or its lower ester with an amino alcohol, to form an amide-alkanol. This ethylenically unsaturated intermediate is then reacted with an $R_F$-iodide under free radical conditions and the product is then dehydrohalogenated with a base. This process for the preparation of the perfluoroalkyl amidoalkyl alcohol of formula I proceeds in a high overall yield.

The perfluoroalkyl amidoalkyl alcohol of formula I can be used to synthesize a variety of fluorinated derivatives by the reaction of fluoroalkylamido alcohol I with alcohol reactive compounds.

Another aspect of the present invention is the provision of novel acrylate or methacrylate monomers of formula II

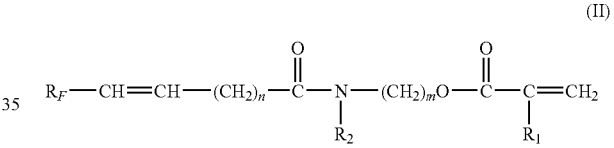

wherein
$R_F$ is a straight or branched-chain perfluoroalkyl group containing 4 to 20 carbon atoms,
$R_1$ is hydrogen or methyl,
$R_2$ is H or an alkyl group with 1 to 4 carbon atoms, and
m and n are, independently of each other, an integer from 2 to 11.

Other aspects of the present invention are polymers and copolymers derived from the acrylate or methacrylate monomers of formula II, their use to impart water, oil and grease resistance to the resulting treated paper, textiles and hard surfaces such as masonry and wood. The residual double bond can be used for crosslinking of the final polymer.

Perfluoroalkyl substituents which are attached to a long-chain hydrocarbon moiety, such as an undecylenic group, exhibit improved surface activity and improved effectiveness as oil repellents, possibly because such long-chain hydrocarbon groups, by their inter-chain interactions, aid in the orientation of the very poorly interacting $R_F$-groups. Hydrogen bonding through the amido groups in the perfluoroalkyl amide-alkyl moiety further promotes a stable linear alignment of the long hydrocarbon-fluorocarbon chains and thereby contributes to the low free surface energy of coatings required for good water and oil repellencies.

DETAILED DISCLOSURE

One aspect of the present invention is provision of a novel fluoroalkyl amidoalkyl alcohol of formula I $$R_F-CH=CH-(CH_2)_n-\overset{O}{\underset{}{C}}-\underset{R_2}{N}-(CH_2)_mOH \quad \text{(I)}$$

wherein $R_F$ is a straight or branched-chain perfluoroalkyl group containing 4 to 20 carbon atoms, $R_1$ is hydrogen or methyl, $R_2$ is hydrogen or an alkyl group with 1 to 4 carbon atoms, and m and n, independently of each other, are an integer from 2 to 11.

The perfluoroalkyl moiety $R_F$ may be a single perfluoroalkyl group, for example perfluorohexyl, or a mixture of such groups, for example a mixture of $C_4F_9-$, $C_6F_{13}-$, $C_8F_{17}-$, $C_{10}F_{21}-$, $C_{12}F_{25}-C_{14}F_{29}-$ and $C_{16}F_{31}-$ groups.

Preferred compounds according to the present invention include those wherein $R_F$ is saturated and contains 6 to 18 carbon atoms, is fully fluorinated and contains at least one terminal perfluoromethyl group. Most preferably, $R_F$ is a fully fluorinated, linear carbon chain with an average of about 4 to 16 carbon atoms.

Preferably $R_2$ is hydrogen or an alkyl group with 1 to 2 carbon atoms, preferably 1.

Preferably n is an integer from 2 to 11, preferably 8, and m is an integer from 2 to 6, especially 2 or 3.

Another aspect of the present invention is the provision of acrylate or methacrylate ester monomers of formula II $$R_F-CH=CH-(CH_2)_n-\overset{O}{\underset{}{C}}-\underset{R_2}{N}-(CH_2)_mO-\overset{O}{\underset{}{C}}-\underset{R_1}{C}=CH_2 \quad \text{(II)}$$

wherein $R_F$ is a straight or branched-chain perfluoroalkyl group containing 4 to 20 carbon atoms, $R_1$ is hydrogen or methyl, $R_2$ is H or an alkyl group with 1 to 4 carbon atoms, and m and n are, independently of each other, an integer from 2 to 11.

The preferences for $R_1$, $R_2$, m, n and $R_F$ are as previously defined for formula I.

Another aspect of the invention is the preparation of fluorochemical copolymers from a monomer mixture comprising a fluoroalkyl amidoalkyl (meth)acrylate monomer of formula II, and the use of these fluorochemical copolymers as internally or externally applied water, oil- and grease proofing paper sizes which impart, in addition to oil resistance, excellent water resistance.

In one embodiment the copolymers are prepared from an $R_F$-amidoalkyl (meth)acrylate of the formula II and other ethylenically unsaturated monomers copolymerized in the following percentages by weight, relative to the total weight of the copolymers:

a) 45-90% by weight of a monomer of formula II $$R_F-CH=CH-(CH_2)_n-\overset{O}{\underset{}{C}}-\underset{R_2}{N}-(CH_2)_mO-\overset{O}{\underset{}{C}}-\underset{R_1}{C}=CH_2 \quad \text{(II)}$$

wherein $R_F$ is a straight or branched-chain perfluoroalkyl group containing 4 to 20 carbon atoms, $R_1$ is H or $CH_3$, $R_2$ is H or an alkyl group with 1 to 4 carbon atoms, and m and n are, independently of each other, an integer from 2 to 11; and b) 5-30% by weight of a monomer of formula III $$(R_2)_2N-(CH_2)_k-X_1-C(=O)-C(R_1)=CH_2 \quad \text{(III)}$$

in which the nitrogen atom is partially or completely quaternized or in the form of a salt and $X_1$ is O or $N(R_2)$ and wherein $R_1$ and $R_2$ are defined as above, each $R_2$ is the same or different, and k is 2 to 4; and c) 0-10% by weight of at least one copolymerizable nonfluorinated vinyl monomer.

Preferably, $R_F$ is a straight chain perfluoroalkyl group with 4-16 carbon atoms, $X_1$ is oxygen, and $R_1$, $R_2$ and n are as defined above.

Especially preferred are copolymers in which the monomers are copolymerized in the following percentages by weight, relative to the total weight of the copolymers:

a) 65-85% by weight; b) 5-30% by weight and c) 0-10% by weight.

A mixture of compounds of the formula II with $R_F$ chain-lengths of 4 to 16 carbon atoms is advantageously employed to prepare the inventive copolymers. In one especially preferred embodiment the monomer of the formula II used to prepare the polymers of this invention is an $R_F$-acrylate which has a chain-length distribution of $R_F$-chains of 13±2% $C_6F_{13}$, 48±2% $C_8F_{17}$, 23±2% $C_{10}F_{21}$ and 1.6% $C_{12}F_{25}$ or higher.

Preferred compounds of the formula III are N,N-dimethylaminoethyl (meth)acrylate; N,N-diethylaminoethyl (meth)acrylate; N,N-dimethylaminopropyl methacrylamide and N-tert. butylaminoethyl methacrylate and their salts.

Useful as co-monomers (c) are a large number of commercially available acrylates and methacrylates, as well as styrene; but preferably methyl methacrylate, N-methylol acrylamide, 2-hydroxyethyl methacrylate, acrylic acid, glycidyl methacrylate, vinylidene chloride, vinyl acetate, 1-vinyl-2-pyrrolidinone, acrylonitrile, methacrylonitrile, vinyl chloride, vinylidene chloride and 1-vinyl-2-pyrrolidinone.

The perfluoroalkyl amidoalkyl alcohol of formula I can be synthesized by reacting a linear terminally unsaturated $C_5$-$C_{14}$monocarboxylic acid or its lower ester with an amino alcohol of the formula III $$HN-\underset{R_2}{|}(CH_2)_mOH \quad \text{(III)}$$

to form an amide-alkanol of the formula Ia

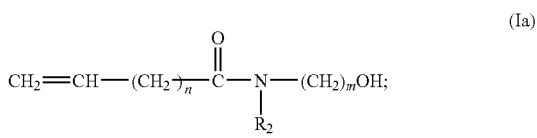

reacting this ethylenically unsaturated intermediate with an $R_F$-iodide using a free radical generating mechanism; then dehydrohalogenating this intermediate with an alkali metal hydroxide, wherein $R_F$, $R_2$, m and n are as defined above.

Preferably the first reaction step is carried out without a solvent, by heating the mixture at a temperature of 40° C. to 180° C. for a period of about 1 to 5 hours. Linear terminally unsaturated monocarboxylic acids such as 4-pentenoic acid and 10-undecenoic acid are preferred. In a second step this ethylenically unsaturated intermediate is reacted with an $R_F$-iodide using a free radical generating mechanism. The intermediate is then subjected to dehydrohalogenation using an alkali metal hydroxide such as sodium or potassium hydroxide.

The addition of an $R_F$-iodide to an olefin proceeds readily in the presence of a free radical initiator such as an azo compound or peroxide at conventional initiation temperatures of 35 to 150° C. However, in the presence of small amounts of aqueous solutions of sulfite, bisulfite or dithionate ions the reaction proceeds faster and gives high conversions.

The general processing conditions for addition of an $R_F$-iodide to an olefin and subsequent dehydrohalogenation to make the compounds of formula I of this invention are described in greater detail in U.S. Pat. No. 5,919,299.

If desired, solvents can be present during the $R_F$-iodide addition reaction. Non-limiting examples include ketones such as acetone, methyl ethyl ketone or methyl propyl ketone, esters such as isopropyl acetate, alcohols such as ethanol or butanol, ethers such as dioxane or di(2-hydroxyethyl)ether, hydrocarbons such as toluene or octane, amides such as dimethylformamide and lactams such as N-methylpyrrolidone.

The dehydrohalogenation of the $R_F$-iodide addition product is generally carried out in water at 50 to 100° C. by reacting the adduct with a strong inorganic base, such as sodium or potassium hydroxide or a strong organic base such as 1,8-diazabicyclo(5.4.0)undec-7-ene (DBU) over a period of several hours. The product is obtained in the non-aqueous phase, which can be separated and washed with water. The solvent can be stripped off; or the product can be isolated as a solution by allowing a clean phase separation to occur between the aqueous and organic phases, followed by drying the organic phase. The mode of isolation will depend on the specific product. Trans olefins are formed predominately, with the cis-/trans ratio being determined by NMR.

The acrylate or methacrylate monomers of formula II can be prepared by the reaction of the $R_F$-amide-alkanol with acryloyl or methacryloyl chloride in the presence of a base such as triethylamine to trap the hydrogen chloride formed. Other methods such as transesterification using a tin catalyst and other procedures can be utilized to synthesize the acrylate and methacrylate esters of formula II.

The copolymers according to the invention are prepared by free radical polymerization of the monomer mixtures described above in an aqueous emulsion or in a solvent. For emulsion polymerization water-soluble co-solvents are commonly used to aid migration of the otherwise insoluble $R_F$-monomers through the aqueous phase. Useful co-solvents include acetone and methanol. Suitable free radical initiators include azo compounds and water-soluble peroxides, such as potassium persulfate. In another variation of the polymerization in an aqueous medium, the $R_F$-monomer is first emulsified in water using a surfactant and a homogenizer, followed by copolymerization with the other monomers.

The preferred method for making the polymers of this invention however is solution polymerization. Useful solvents are ketones such as acetone, methyl isobutyl ketone and methyl ethyl ketone, esters such as isopropyl acetate, alcohols such as methanol, ethanol and isopropanol, and aromatic hydrocarbons such as toluene.

The polymerization is typically carried out at temperatures of from about 50 to 100° C. using a free radical initiator, typically a peroxide or azo compound. Useful initiators include benzoyl peroxide, 1,2-azo-bis-isobutyronitrile (AIBN) and 1,2-azo-bis-(2-methylbutane nitrile) (VAZO-67).

A chain-transfer agent can be present, such as an alkyl thiol, in amounts of from 0.01 to 1 mole percent.

After the polymerization is complete, the solution is readily transformed into a cationic aqueous dispersion or solution by adding an aqueous solution of an organic acid such as acetic acid; and then distilling off the organic solvent to provide a dispersion or solution conveniently having a solids content of between 20% and 40% by weight.

The fluorochemical copolymers prepared from a monomer mixture comprising a fluoroalkyl amidoalkyl (meth)acrylate monomer of formula II according to the invention are useful as coatings on porous substrates such as paper and textiles, or on hard substrates such as wood, metal or masonry. In the paper industry, their main usefulness is based on their ability to impart oil and grease resistance to paper that is used for food packaging or for any other type of application where resistance to oily substances is required.

Thus, another aspect of the present invention relates to a method of imparting oil and grease resistance to paper, which comprises incorporating an amount of a copolymer according to this invention that is effective to impart oil and grease resistance into the paper.

The application of the copolymer to paper can either be to the dry paper through a coating process via a size-press (external paper sizing) or by addition of a solution or emulsion of the copolymer to an aqueous pulp (internal paper sizing). The level of application in either case is preferably in the range of 0.02 to 1% by weight of the copolymer, based on the weight of the dry paper or pulp, corresponding roughly to incorporation of 0.01 to 0.5% by weight of fluorine into the paper or pulp.

Another aspect of the present invention relates to a method of imparting water, oil and grease resistance to textile materials, which comprises treating the fabric with 0.2 to 1.0% by weight of a copolymer according to this invention that is effective to impart water, oil and grease resistance onto the textile materials.

Suitable textile materials include cellulosics, especially cotton, polyamides such as nylon, wool and silk, polyesters and polyolefins and blends thereof such as polyester-cotton blends. In one embodiment the textile material is a carpet.

Still another aspect of the present invention relates to a method of imparting oil and grease resistance to hard substrates such as wood, metal or masonry, which comprises applying an amount of a copolymer according to this invention that is effective to impart oil and grease resistance onto the surface of the hard substrate. These waterborne fluorochemical copolymer compositions can be applied to the surface by any convenient ways such as wiping with a sponge or cloth, painting with a brush, spraying, and other means.

The following examples describe certain embodiments of this invention, but the invention is not limited thereto. It should be understood that numerous changes to the disclosed embodiments can be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

The non-limiting examples illustrate how to synthesize the inventive copolymers and describe in detail methods of their application to various substrates. They also demonstrate the good performance of the copolymers on the various substrates.

EXAMPLE 1

The perfluoroalkyl amidoalkyl alcohol of formula I is synthesized by condensation of, e.g. 10-undecenoic acid with an alkanolamine such as ethanolamine or propanolamine. The general procedure for the synthesis is given below.

Synthesis of a Perfluoroalkyl Amidoalkyl Alcohol

Into a 100 ml three-necked flask fitted with a mechanical stirrer, thermometer, distillation condenser, 20.2 g (0.107 moles) of 10-undecenoic acid is placed. The reaction flask is heated to 50° C., followed by the slow addition of 9.8 g (0.16 moles) of ethanolamine. The reaction temperature is slowly increased to 180° C. and held at this temperature for 4 hours. The progress of the reaction is followed by gas chromatography. After 4 hours 1.8 g (95% of theoretical value) of water is collected. The reaction mixture is cooled to room temperature; the tan colored product is dissolved in ethanol, and then poured into water. The white precipitate of amidealkanol obtained is filtered, washed with water and dried to give 24.0 g (Yield=97%) of a white powder.

$^1$H NMR δ: 5.85 (m, 1H), 5.0 (m, 1H), 4.9 (m, 1H), 3.6 (t, 2H), 3.3 (m, 2H), 2.2 (2H), 2.1 (q, 2H), 1.6 (b, 2H), 1.4 (t, 2H), 1.35 (8H) ppm. $^{13}$C NMR δ: 173, 140, 115, 62, 43, 36, 34, 30, 29.8, 25 ppm.

To a 100 ml three necked flask fitted with a mechanical stirrer, condenser and nitrogen purge inlet; 10.0 g (44 mmoles) of amidealkanol from above; 11 g of n-propanol, 5 g of water and 27.0 g (44 mmoles) of Tel AN (DuPont's Zonyl Tel AN with a homologue distribution of 53.0% $C_8F_{17}I$, 30.6% $C_{10}F_{21}I$, 11.7% $C_{12}F_{25}I$, 3.6% $C_{14}F_{29}I$, and 1.0% $C_{16}F_{33}I$) are added. The mixture is stirred at about 74° C. To the reaction mixture 0.8 g (4.2 mmoles) of sodium metabisulfite and 0.25 g (1.3 mmoles) of VAZO-67 are added. The progress of the reaction is followed by gas chromatography. After 3 hours no Tel AN is detected. At about 50° C., 5.0 g of 50% NaOH solution is added slowly to the contents of the flask and the mixture is stirred at about 70° C. After 3 hours, gas chromatography shows that dehydrohalogenation is complete. The reaction mixture is cooled to 60° C.; then 15.0 g of toluene and 10.0 g of water is added. After stopping agitation the top product layer is removed and washed twice with 20.0 g portions of water. The solvent is removed on a rotary evaporator. Then the product is dried under high vacuum at 50° C., to give the compound of formula (101)

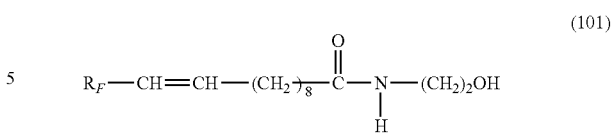

as a cream colored tacky solid having 48 weight % fluorine.

$^1$H NMR δ: 6.4 (1H, m), 5.7 (1H, m), 3.6 (2H, m), 3.3 (2H, m), 2.2 (4H, m), 1.6 (2H, b), 1.4 (2H, b), 1.3 (8H) ppm. $^{13}$C NMR δ: 176, 117 (m), 144 (m), 110-120 (multiple lines, $CF_3$ and $CF_2$ groups), 61, 26, 43, 37, 33, 30.2, 29.9, 27 ppm.

EXAMPLE 2

Synthesis of a Perfluoroalkyl Amidoalkyl Acrylate

To a 100 ml three necked flask fitted with a mechanical stirrer, and a condenser; 8.45 g (11.8 mmoles) of perfluoroalkyl-substituted alcohol (101); 30.0 ml of MIBK, and 2.0 g (20 mmoles) of triethylamine are placed. To the reaction mixture at 10° C., under nitrogen atmosphere, 1.5 g (16.6 mmoles) of acryloyl chloride in 5 ml of MIBK is added slowly, and then the reaction mixture is stirred at room temperature for 5 hours. A saturated aqueous NaCl solution is then added and the mixture is allowed to settle. The top layer containing the product is removed and then washed once with 30.0 g saturated aqueous NaCl. The solvent is evaporated on a rotary evaporator at 65° C. and then at high vacuum to give 8.2 g (yield=94%) of the compound of formula (102)

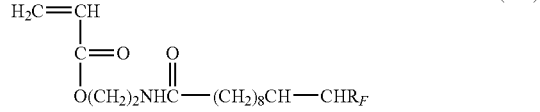

as a brown colored solid of formula (101) having 43% fluorine.

EXAMPLE 3

A flask fitted with a reflux condenser, thermometer, and a mechanical stirrer is charged with 5.0 g (6.37 mmoles) of the perfluoroalkyl acrylate of EXAMPLE 2, 2.0 g (10.8 mmoles) N,N-diethylaminoethyl methacrylate, 0.2 g (3 mmoles) methyl methacrylate and 5.0 g methyl isobutyl ketone. The flask is purged with nitrogen and 0.1 g VAZO-67 is added. The polymerization is performed by stirring the mixture for 5 hours at a temperature between 74 and 78° C. To the polymerization mixture an aqueous solution of acetic acid (0.1 g acetic acid in 30 g water) is then added, and the mixture is stirred for 15 minutes. The mixture is then transferred to a round-bottomed flask and methyl isobutyl ketone is removed under vacuum, resulting in a yellow aqueous copolymer solution.

EXAMPLES 4 TO 6

The procedure of EXAMPLE 3 is used to prepare EXAMPLES 4 to 6, using azobisisobutyronitrile as the initiator and the comonomer weight ratios listed below.

| | Composition of Copolymers, in weight percent | | | |
|---|---|---|---|---|
| EXAMPLE | $R_F$-monomer | Amino (meth)acrylate | Methyl methacrylate | Other |
| 3 | 69 | 28 | 3 | — |
| 4 | 83 | 17 (DEEM) | — | — |
| 5 | 89 | 5 | 2 | 4 (NVP) |
| 6 | 75 | 22 | 3 | — |

DEEM = diethylaminoethyl methacrylate
NVP = 1-Vinyl-2-pyrrolidinone

EXAMPLE 6

The procedure of EXAMPLE 3 is repeated, using 2.4 g n-dodecyl mercaptan as chain-transfer agent.

The following example shows the performance of the novel $R_F$-polymers as internal paper sizes.

EXAMPLE 7

The compounds of EXAMPLES 3-6 were tested as described below.

Internal Size Application and Testing:

Paper plates of 10 inch diameter were made on a small scale paper plate-making machine, supplied by the CHINET Company. This machine consists of a rotating element bearing three radially attached dies, one called the "forming die" which in step 1 is immersed in the pulp and through which the pulp is filtered onto the plate by vacuum; after a ¼ revolution the plate reaches step 2, a die called the "vacuum die" which molds and dries the plate by suction and heat, and in two more ¼ revolutions reaches two more cross-head dies which further dry the plate by heat. The final dryness of the plate is influenced by the strength of the vacuum and the drainage characteristics of the pulp, and by the temperatures of the various dies. A minimum dryness of at least 94% (i.e. 6% water or less) is desirable, otherwise the paper plates loose wet strength.

In the following experiments these conditions were used:
Machine Settings: 10 inch plates;
Target dryness: 95-96%; vacuum die: 300° F./1.XH: 385°F./2.XH: 375° F.
Wet End:
Pulp supplied by the CHINET Company, 3 pounds/trial run, containing as wet-end chemicals, added in 40 sec intervals to the stirred pulp, in order of addition:
Nalco 7607—cationic retention aid and coagulant (NALCO CHEM. Co.), 8 pounds/ton;
Alkyl-ketene dimer (AKD) Water repellent (HERCULES Corp.), 6 pounds/ton the fluorochemical polymeric size: calculated to give 0.1 weight % F addon;
Nalco 625—anionic coagulant (NALCO CHEM. Co.), 1 pound/ton.
Tests: two tests were carried out:
Hot Saline Solution and Hot Oil test:
Procedure:
1. Weigh paper plate.
2. Pour either 2% saline at 72° C. or Mazola corn oil at 99° C. onto plate, enough to fully cover surface.
3. After 5 minutes, pour off solution, wipe plate dry with paper towels and reweigh.
4. Calculate weight % absorption and rate visually the degree of penetration (R): R=0=>50%; 1=25-50%; 2=<25%; 3=none.

Percent absorption is the more accurate measure of water/oil holdout performance.

The finished plates were tested "off machine", i.e. shortly after made and after 24 hours. Plate dryness "off-machine" was determined gravimetrically.

The test results are shown in the following table.

| | | Hot Oil | | Hot Water Hold-Out (2% Saline) | | |
|---|---|---|---|---|---|---|
| | | Hold-Out | | off machine | | 24 hrs. |
| Cpd. of Ex. No. | % F added | R | % abs | R | % abs | R | % abs |
| 3 | 0.07 | 3 | 1 | 15 | 3 | 3 |
| 3 | 0.15 | 3 | 1 | 15 | 3 | 3 |

The results demonstrate superior oil and water hold-out performance at two different fluorine levels.

EXAMPLE 8

The following example shows the usefulness of the novel copolymers as external paper sizes.

External Size Application:

The neutralized test solutions are added to a 4% aqueous solution of paper maker's starch (Stayco M, oxidized starch, from Staley Corp.) and then applied to unsized paper by padding (paper dipped through starch solution, and passed through single nip rollers). The resulting sheets are dried at ambient conditions for 15 minutes, then 3 minutes at 200° F. (97° C.) in an "Emerson Speed Drier" (heated metal plate with canvas cover).

Oil and Grease Resistance Tests:

Oil Kit Test:
The oil repellency of the surface is determined by using the TAPPI UM 557 OIL KIT TEST, which consists of determining with which of twelve castor oil-heptane-toluene mixtures having decreasing surface tensions penetration occurs within 15 seconds; ratings go from 1, lowest, up to 12.

Ralston-Purina (RP2) Test:
Grease resistance is determined with the Ralston-Purina test for pet food materials; RP-2 Test, Ralston-Purina Company, Packaging Reference Manual Volume 06, Test Methods. In summary: cross-wise creased test papers are placed over a grid sheet imprinted with 100 squares. Five grams of sand are placed in the center of the crease. A mixture of synthetic oil and a dye for visualization is pipetted onto the sand and the samples are maintained at 60° C. for 24 hours. Ratings are determined by the percentage of stained grid segments, using at least two samples.

Turpentine Test, according to TAPPI T454 om-94, a preliminary test to determine rates at which oil or grease can be expected to penetrate the paper.

Water and Alcohol Resistance Tests

Cobb Size Test:
Water resistance is determined using the Cobb Sizing test, as described in TAPPI T 441 om-90.

IPA Resistance Test:
In this test drops of isopropanol-water mixtures are placed on paper, and after 3 minutes the under side of the paper is monitored for penetration; if no penetration has occurred, a mixture with the next higher IPA content is applied. The rating is based on the highest % by weight IPA which does not penetrate. Ratings are based on 5% IPA increments. The results are shown in the following table.

| Cpd. of Ex. No. | % F | Oil Kit | RP-2 | Turpentine Test | Cobb Size Test | IPA Hold-out Test |
|---|---|---|---|---|---|---|
| 3 | 0.09 | 8 | 4x0 | 1800+ | 21 | 10 |
| 4 | 0.1 | 10 | 4x0 | 1800+ | 20 | 40 |
| P-514[1] | 0.12 | 12 | 4x0 | 1800+ | 22 | 40 |
| P-208[2] | 0.10 | 10 | 4x0 | 1800 | 72 | 0 |
| FC-845[3] | 0.10 | 10 | 4X0 | 1800+ | 22 | 40+ |

[1] Ciba Lodyne ® P-514, is a commercial polymeric fluorinated paper size available from Ciba Specialty Chemicals Corp.
[2] Ciba Lodyne ® P-208E is a commercial phosphate ester fluorinated paper size from Ciba Specialty Chemicals Corp.
[3] Scotchguard ® FC-845 is a commercial polymeric fluorinated paper size from 3M Corp.

I claim:

1. An alcohol of formula I,

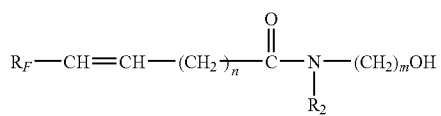

wherein $R_F$ is a straight or branched-chain perfluoroalkyl group containing 4 to 20 carbon atoms, $R_2$ is hydrogen or an alkyl group with 1 to 4 carbon atoms, and m and n are, independently of each other, an integer from 2 to 11.

2. An alcohol according to claim 1, wherein $R_F$ is saturated and contains 6 to 18 carbon atoms, is fully fluorinated and contains at least one terminal perfluoromethyl group.

3. An alcohol according to claim 1, wherein, $R_F$ is a fully fluorinated, linear carbon chain with an average of about 4 to 16 carbon atoms, $R_2$ is hydrogen or an alkyl group with 1 to 2 carbon atoms, n is an integer from 5 to 10, and m is an integer from 2 to 6.

4. An alcohol according to claim 3, wherein $R_F$ is a fully fluorinated, linear carbon chain with an average of about 4 to 16 carbon atoms, $R_2$ is hydrogen, n is 8, and m is an integer from 2 to 3.

5. A process for the preparation of an alcohol according to claim 1, which comprises a) reacting a linear terminally unsaturated $C_5$-$C_{14}$ monocarboxylic acid or its lower ester with an amino alcohol of the formula III

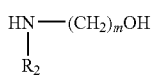

to form an amide-alkanol of the formula Ia

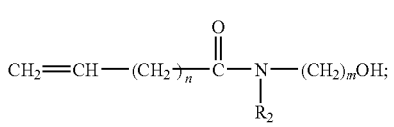

b) reacting the ethylenically unsaturated intermediate of the formula Ia with an $R_F$-iodide using a free radical generating mechanism; and then c) dehydrohalogenating the intermediate from step b) with an alkali metal hydroxide, wherein $R_F$, $R_2$, m and n are as defined in claim 1.

* * * * *